(12) United States Patent
Boisseau et al.

(10) Patent No.: US 9,427,599 B1
(45) Date of Patent: Aug. 30, 2016

(54) MULTI-RESOLUTION DETECTORS FOR MEASURING AND CONTROLLING A CHARGED PARTICLE PENCIL BEAM

(71) Applicant: Pyramid Technical Consultants, Inc., Lexington, MA (US)

(72) Inventors: R. Paul Boisseau, Waltham, MA (US); Andrew Dart, Swampscott, MA (US); John Gordon, Henfield (GB); Kan Ota, Bedford, MA (US)

(73) Assignee: Pyramid Technical Consultants Inc., Lexington, MA (US)

( * ) Notice: Subject to any disclaimer, the term of this patent is extended or adjusted under 35 U.S.C. 154(b) by 1 day.

(21) Appl. No.: 14/632,270

(22) Filed: Feb. 26, 2015

(51) Int. Cl.
  *G01T 1/24* (2006.01)
  *A61N 5/10* (2006.01)
(52) U.S. Cl.
  CPC ............ *A61N 5/1048* (2013.01); *A61N 5/1077* (2013.01); *A61N 2005/1074* (2013.01)
(58) Field of Classification Search
  CPC ....... G01T 1/2935; G01T 1/29; G01T 1/241; G01T 3/008
  See application file for complete search history.

(56) References Cited

U.S. PATENT DOCUMENTS

| | | | |
|---|---|---|---|
| 6,362,484 B1 | 3/2002 | Beyne et al. | |
| 6,847,036 B1* | 1/2005 | Darling | H01J 49/10 250/291 |
| 9,293,310 B2* | 3/2016 | Boisseau | H01J 47/02 |
| 2005/0116174 A1* | 6/2005 | Berdermann | G01T 1/26 250/370.01 |
| 2007/0075252 A1 | 4/2007 | Misawa | |
| 2008/0061245 A1 | 3/2008 | Yamamoto | |
| 2010/0265078 A1 | 10/2010 | Friedman | |
| 2015/0001411 A1 | 1/2015 | Friedman et al. | |

OTHER PUBLICATIONS

European Patent Office, "Extended European Search Report, Appl. No. 16000424", Jul. 1, 2016, EPO.

* cited by examiner

*Primary Examiner* — Kiho Kim
(74) *Attorney, Agent, or Firm* — Intrinsic Law Corp.; Ibrahim M. Hallaj

(57) ABSTRACT

A multi-resolution detector includes a high-resolution pixelated electrode and a low-resolution pixelated electrode. The high-resolution pixelated electrode includes a plurality of sub-arrays of first pixels. Each respective first pixel at each relative position in each sub-array is electrically connected in parallel with one another. The low-resolution pixelated electrode includes a plurality of second pixels. A control system receives as inputs an output from each pixelated detector. The control system uses the inputs to determine a physical position and a transverse intensity distribution of an incident charged particle pencil beam at the resolution of the high-resolution pixelated electrode.

24 Claims, 13 Drawing Sheets

MULTI-RESOLUTION DETECTORS FOR MEASURING AND CONTROLLING A CHARGED PARTICLE PENCIL BEAM

TECHNICAL FIELD

This invention relates generally to charged particle pencil beam therapy. Specifically, systems and methods are disclosed for providing enhanced monitoring, diagnostics, and/or control of charged particle pencil beams using multi-resolution detectors.

BACKGROUND

Radiation therapy systems can be used to provide treatment to patients suffering a variety of conditions. Radiation therapy can be used to perform selective cell destruction, useful in controlling cancers by treating tumorous tissue. Particle therapy is a form of radiation therapy that uses light ions to destroy targeted cells. Particle therapy can be an efficacious way to selectively destroy targeted cells because light ions have unique dosimetric characteristics compared to other ionizing radiation, such as electrons or high energy photons. Light ions deposit most of their energy near the end of their path through a tissue. Because the dose provided by an ion is concentrated at a "Bragg peak" around the area where the ion stops, the dose to healthy tissue proximal to the target region may also be reduced. The well-defined maximum range of the ions ensures that tissue on the distal side of the target receives a negligible dose of radiation.

A particular type of particle therapy is proton therapy, in which the light ions species are protons. Protons are a convenient particle to use as they are the lightest ion species that provide the advantages described above.

One technique for delivering particle therapy is called pencil beam scanning. In this technique, the light ion beam remains narrowly collimated in a "pencil beam" and is steered in angle (deflection) and adjusted in range (energy) to deposit the dose as a small spot at a precise volume within the patient. Thus, complex volumetric shapes (e.g., organs) can be treated with a pencil beam without irradiating the surrounding tissue.

This approach is potentially very accurate. However, the small spot sizes can create the risk of uneven dose placement or "cold spots" should there be patient movement between exposures. In addition, precise measurement and control of the location and dosage (e.g., intensity distribution over time) of the spot is critical for safe and effective treatment of a patient.

Existing pixelated ionization detectors for measuring the location, transverse intensity distribution, and dosage of the beam spot typically have channel counts up to around 1,000. Such detectors either have low resolution over a large active area or high resolution over a small active area. While enhanced resolution at large area is possible, it can only be done at the cost increasing the number of readout electronic channels. This increases the cost of the device and requires an expensive high-capacity data link to transmit the large volume of data from the pixels to a receiving device at high update rates.

Accordingly, there is a need for a high-resolution detector that can accurately determine radiation dose and beam position over a large area using less expensive components while maintaining high update rates.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In an aspect, the invention includes a multi-resolution detector disposed at or near (e.g., proximal to) an isocenter plane. The multi-resolution detector includes a first pixelated electrode and a second pixelated electrode. The first pixelated electrode comprises a plurality of sub-arrays of first pixels that detect an electrical current created by an incident charged particle pencil beam. Each respective first pixel at each relative position in each sub-array is electrically connected in parallel with one another, such that the first pixelated electrode dynamically generates a first output representing a combined electrical output of the respective first pixels from the sub-arrays. The first pixels can have a first size corresponding to a first resolution.

The second pixelated electrode includes a plurality of second pixels. The second pixelated electrode is configured to dynamically generate a second output representative of an approximate physical position of the charged particle pencil beam in a plane substantially parallel to the isocenter plane. The second pixels can have a second size corresponding to a second resolution. The first pixels can have a smaller size than the second pixels thus resulting in a higher resolution first pixelated electrode and a lower resolution second pixelated electrode.

A diagnostic control system includes a memory and a processor. The diagnostic control system is configured to receive as inputs the first output and the second output and to determine an actual position and an actual transverse intensity distribution of said charged particle beam based on the first and second outputs. The actual position and the actual intensity distribution have the resolution of the first pixelated electrode (e.g., high resolution).

In another aspect, the invention includes a multi-resolution detector system disposed at or near (e.g., proximal to) an isocenter plane. The multi-resolution detector system includes a first pixelated detector and a second pixelated detector. The first pixelated detector includes a first pixelated electrode that includes a plurality of sub-arrays of first pixels that detect an electrical current created by an incident charged particle pencil beam. Each respective first pixel at each relative position in each sub-array is electrically connected in parallel with one another, such that the first pixelated electrode dynamically generates a first output representing a combined electrical output of the respective first pixels from the sub-arrays. The first pixels can have a first size corresponding to a first resolution.

The second pixelated detector includes a second pixelated electrode that includes a plurality of second pixels. The second pixelated electrode is configured to dynamically generate a second output representative of an approximate physical position of the charged particle pencil beam in a plane substantially parallel to the isocenter plane. The second pixels can have a second size corresponding to a second resolution. The first pixels can have a smaller size than the second pixels thus resulting in a higher resolution first pixelated electrode and a lower resolution second pixelated electrode.

A diagnostic control system includes a memory and a processor. The diagnostic control system is configured to receive as inputs the first output and the second output and to determine an actual position and an actual transverse intensity distribution of said charged particle beam based on the first and second outputs. The actual position and the actual intensity distribution have the resolution of the first pixelated electrode (e.g., high resolution).

In another aspect, the invention includes a method of characterizing a charged particle pencil beam. The method includes receiving a combined electrical output generated by a charged particle pencil beam with a first pixelated electrode. The first pixelated electrode comprises a plurality of sub-arrays of first pixels having a first resolution. Each respective first pixel at each relative position in each sub-array is electrically connected in parallel with one another.

The method also includes determining an approximate physical position of the charged particle pencil beam with electrical output data from a second pixelated electrode. The second pixelated electrode comprises a plurality of second pixels having a second resolution. The second resolution is lower (e.g., larger pixel size) than the first resolution (e.g., smaller pixel size).

The method also includes calculating an actual physical position and an actual transverse intensity distribution of the charged particle pencil beam using the combined electrical output from the first pixelated electrode and the approximate physical position determined from the second pixelated electrode. The actual physical position and the actual transverse intensity distribution are determined at the first resolution, which is higher/finer than the second resolution.

In another aspect, the invention includes an integrated multi-resolution detector. The multi-resolution detector comprises a first pixelated electrode, a second pixelated electrode, and a high-voltage plane. The first pixelated electrode is disposed in a first plane. The first pixelated electrode includes a plurality of sub-arrays of first pixels to detect an electrical current created by a charged particle pencil beam. Each respective first pixel at each relative position in each sub-array is electrically connected in parallel with one another. The first pixelated electrode dynamically generates a first output representing a combined electrical output of the respective first pixels from the sub-arrays.

The second pixelated electrode is disposed in a second plane. The second pixelated electrode includes a plurality of second pixels. The second pixelated electrode is configured to dynamically generate a second output representative of a physical position of the charged particle pencil beam in the second plane. The second pixelated electrode has a second resolution (e.g., larger pixel size) less than a first resolution (e.g., smaller pixel size) of the first pixelated electrode.

The high-voltage plane is disposed between the first and second pixelated electrodes. The first plane, the second plane, and the high-voltage plane are substantially parallel to one another.

IN THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DETAILED DESCRIPTION

Figure 1:
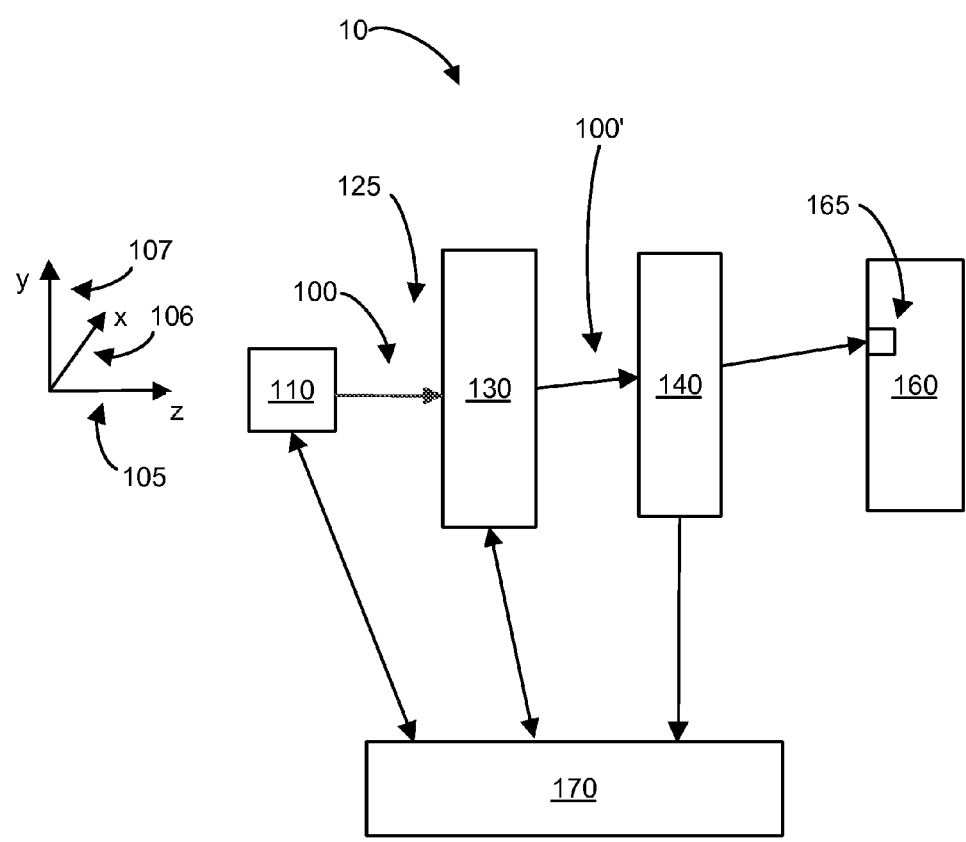
FIG. 1 illustrates a block diagram of a pencil beam scanning (PBS) system.

The present disclosure relates to systems and methods in the application of particle beam therapy. Specifically, methods comprise novel manufacturing of position sensing electrodes. Systems comprise environmental controls, interlocks, interfaces, and accurate monitoring of particle beams and means of measuring beam profiles with good spatial resolution and good time resolution. The proceeding discussion is demonstrative of proton therapy systems; however, the present invention is not beyond the scope of other beams used for therapeutic purposes, such as, energetic photons, positive ions, neutrons or other hadrons or leptons.

The disclosure generally describes a detector system where the readout electrodes are in close proximity along the direction of propagation of the beam, such that both readout electrodes respond approximately equally to the same transverse intensity distribution. One skilled in the art will appreciate alternative configurations and embodiments that apply the principles described herein. For example, the readout electrodes can be physically separated in their own detector systems. Additional processing can be performed for such alternative configurations to address the trajectory angle(s) of the beam and/or the magnification of the beam due to beam divergence.

Improved resolution of the location and/or the transverse intensity distribution of a pencil beam can be achieved through the combination of a high-resolution ionization chamber electrode and a low-resolution ionization chamber electrode. The high-resolution electrode includes a plurality of sub-arrays that each includes pixels having a first size resulting in a first resolution. The sub-arrays are electrically connected in parallel with one another such that all the first pixels in each sub-array are connected, all the second pixels in each sub-array are connected, and so on for all the sub-array pixels. The output signal of the high-resolution electrode includes data that represents a pixel-by-pixel summed electrical output of all the sub-arrays.

The low-resolution electrode includes a plurality of pixels having a second size. The second size is larger than the first size such that the first resolution is greater than the second resolution. The output signal of the low-resolution electrode includes data that represents a physical location of the pencil beam spot.

A control system receives the output signals of the high- and low-resolution electrodes. The control system can use the data from the low-resolution electrode to determine the approximate location of the intensity centroid of the pencil beam spot. The control system can then determine the specific sub-array(s) in the high-resolution electrode that correspond with the approximate physical location measured by the low-resolution electrode. The control system can then re-map the data from the high-resolution electrode to reconstruct the intensity distribution of the pencil beam spot in physical space, at the full resolution of the high-resolution electrode. Using the high-resolution physical location data, the control system can generate data for quality assurance of the particle beam properties and/or control signals to modify the location and/or the intensity of the charged particle beam.

An advantage to this system is that the physical location and/or transverse intensity distribution of the charged particle pencil beam can be determined at a high resolution while using less complex and less expensive components. This advantage is especially evident for detectors which use pixelated sensing elements as opposed to strip elements. Pixelated elements are beneficial because they provide a true two-dimensional sampling of the beam intensity distribution rather than one-dimensional projections. This can reveal features in the intensity distribution which are undetectable by strip sampling. However, pixelated elements need additional read-out electronics than strip elements to obtain the same spatial resolution, so pixelated elements are generally more complex and expensive than strip elements.

By electrically connecting the equivalent pixels in each sub-array of the high-resolution electrode in parallel with one another, less circuitry and readout electronics are required than if each pixel were individually instrumented for readout. For example, to determine the physical location of a beam at 2 mm of resolution over a typical beam scan area of 25 cm×25 cm, one would need a pixelated detector having 15,625 pixels (125 pixels in the "x" direction and 125 pixels in the "y" direction) and an equal number of electronic readout channels. Such a detector would be more expensive to manufacture due to the number of sensitive readout circuits and the high capacity data link needed to read the large volume of data (from the large number of pixels and sensors) at a typical operating frequency for particle therapy systems (e.g., 100 Hz to 5 kHz).

In contrast, the high-resolution pixelated detector described herein can be manufactured for substantially lower cost. If the above-described high-resolution pixelated electrode with 15,625 pixels is configured in 16 sub-arrays comprised of pixels that are electrically connected in parallel with one another, then there is an equivalent of $\frac{1}{16}$ the number of pixels (i.e., about 1,000 pixels). If the associated low-resolution electrode also has about 1,000 pixels over the same beam scan area, then the overall reduction in the number of readout channels is a factor of eight compared to a prior art system with equivalent spatial resolution. Due to the reduction in the number of readout channels, there is a corresponding decrease in the data load on the data link to the control system.

One or more embodiments or implementations are hereinafter described in conjunction with the drawings, where like reference numerals are used to refer to like elements throughout, and where the various features are not necessarily drawn to scale.

FIG. 1 illustrates a block diagram of a pencil beam scanning (PBS) system 10. The system 10 includes a pencil beam generator 110, a magnetic field generator 130, a detector system 140, and a control system 170. The pencil beam generator 110 generates a charged particle pencil beam 100 that travels from the pencil beam generator 110 to the magnetic field generator 130 in a direction substantially parallel to a reference axis 105. The charged particle pencil beam 100 can be a proton beam or a beam of another charged particle such as ions of helium or carbon. The charged particle pencil beam 100 has an energy (typically measured in megaelectron volts or MeV), and an intensity distribution transverse to its direction of travel. In some embodiments, the pencil beam 100 has an energy between 30 and 250 MeV, which can be useful for the therapeutic treatment of tumors and other conditions in a human patient. For a given time interval, the energy of the charged particle pencil beam 100 can be generally constant. However, the energy can vary between time intervals.

The charged particle pencil beam 100 is directed by one or more magnetic fields generated by the magnetic field generator 130. The magnetic field generator 130 can direct and/or deflect the charged particle pencil beam 100 to form a deflected charged particle pencil beam 100' that travels at an angle relative to the reference axis 105 towards a target volume 165 in a patient 160. In some embodiments, the angle between the deflected charged particle pencil beam 100' and the reference axis 105 is small, for example less than or equal to 10 degrees. The target volume 165 can correspond to a portion of a tumor in the patient 160 targeted for treatment. In some embodiments, the magnetic field generator 130 includes a first electromagnet for directing the charged particle pencil beam 100 in a first direction parallel to a first axis 106, which is orthogonal to the reference axis 105 (e.g., a horizontal or "x" direction) and a second electromagnet for deflecting the charged particle pencil beam 100 in a second direction parallel to a second axis 107, which is orthogonal to both the reference axis 105 and the first direction (e.g., the vertical or "y" direction). The first and second magnets can work together or separately to direct the charged particle pencil beam 100 to the model target location 165 in the patient 160, as described above. In addition or in the alternative, the magnetic field generator 130 can include a multipole magnet with pole pieces arranged in a symmetrical pattern centered around the undeflected axis of the charged particle pencil beam 100. Such a multipole magnet or electromagnet can direct the charged particle pencil beam 100 in the first direction and/or the second direction towards the model target location 165, as discussed above. Other variations and arrangements of the magnetic field generator 130 will be apparent to one skilled in the art.

The detector system 140 is configured to track the deflected charged particle pencil beam 100' during patient treatment. The detector system 140 can be one or more ionization detectors, such as a strip ionization detector or a pixelated ionization detector. In some embodiments, the detector system 140 is an integrated multi-resolution pixelated detector as described below. In some embodiments, the detector system 140 includes a first pixelated detector having a first resolution (e.g., first pixel size) and a second pixelated detector having a second resolution (e.g., second pixel size). In some embodiments, the detector system 140 has a negligible energy loss and lateral scattering deflections to the charged particles in the deflected charged particle pencil beam 100'.

The control system 170 is in communication with the pencil beam generator 110, the magnetic field generator 130, and the detector system 140. The control system 170 receives signals representing output data from the pencil beam generator 110, the magnetic field generator 130, and the detector system 140 and provides a feedback control signal to the pencil beam generator 110 and the magnetic field generator 130 as known in the art. The control signal can adjust one or more parameters of the PBS system 10 including the intensity of the charged particle pencil beam 100 and/or the deflection angle of the deflected charged particle pencil beam 100'.

Figure 2:
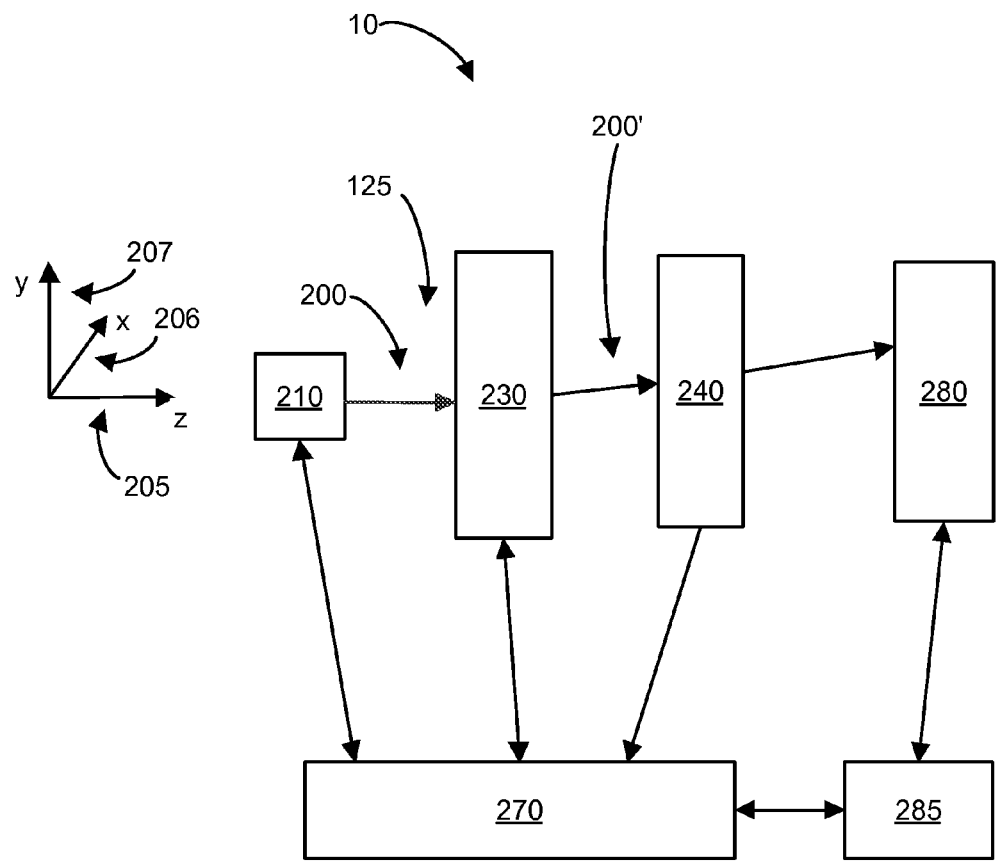
FIG. 2 illustrates a block diagram of a PBS system configured for quality assurance.

FIG. 2 is a block diagram of a PBS system 20 configured for quality assurance measurements. The PBS system 20 includes a pencil beam generator 210, a magnetic field generator 230, a detector system 240, a control system 270, and a diagnostic detector system 280 and a detector control system 285. The diagnostic detector system 280 is located at or near the isocenter plane where the patient would be placed for treatment (e.g., the patient 160 described above). The diagnostic detector system 280 includes a first pixelated detector having a first resolution (e.g., pixel size) and a second pixelated detector having a second resolution (e.g., pixel size). The first resolution is different than the second resolution. In some embodiments, the first resolution is lower (e.g., larger pixel size) than the second resolution. In some embodiments, the first resolution is higher (e.g., smaller pixel size) than the second resolution. In some embodiments, the diagnostic detector system 280 includes a beam stop to measure the kinetic energy and/or total beam current of the beam. The diagnostic detector system 280 can collect data to read out parameters of the deflected beam 200' that are important for accurate patient treatments. Such beam parameters can include the centroid position of the transverse intensity distribution, the beam trajectory angle, the shape of the transverse intensity distribution of the beam, the divergence angles of the envelope of the beam distribution, the total beam current and the beam kinetic energy. Such parameters can be used for quality assurance (e.g., during system setup and/or qualification). In some embodiments, the parameters are sent from the diagnostic system 280 to the control system 270 to modify and/or calibrate the pencil beam generator 210 and/or the magnetic field generator 230.

Figure 3:
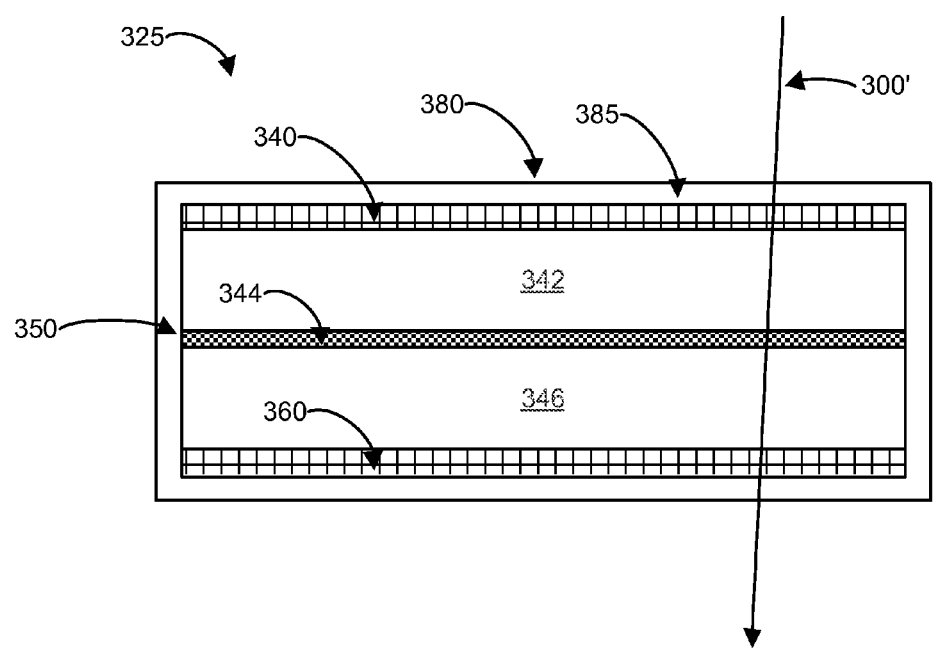
FIG. 3 illustrates a cross-sectional view of a multi-resolution pixelated detector.

The first and second pixelated detectors in the diagnostic detector system 280 can be integrated into a multi-resolution pixelated detector 325 as illustrated in FIG. 3. The multi-resolution pixelated detector 325 includes a first pixelated electrode 340, a first gas gap 342, a high voltage plane 350, a second gas gap 346, and a second pixelated electrode 360, which are disposed in a housing 370. A beam entrance window is disposed on a proximal side of the first pixelated electrode 340. The housing 370 and beam entrance window 380 can provide a clean, dry gas environment. An optional gas gap 385 is disposed between the beam entrance window 380 and the first electrode 340. As illustrated, a deflected charged particle beam 300' passes through the layers of the multi-resolution pixelated detector 325 approximately orthogonal to the respective planes defined by each pixelated electrode 340, 360. The first and second pixelated electrodes 340, 360 have first and second resolutions, respectively. The first resolution can be greater (e.g., smaller pixel size) than the second resolution, or vice versa.

Figure 4:
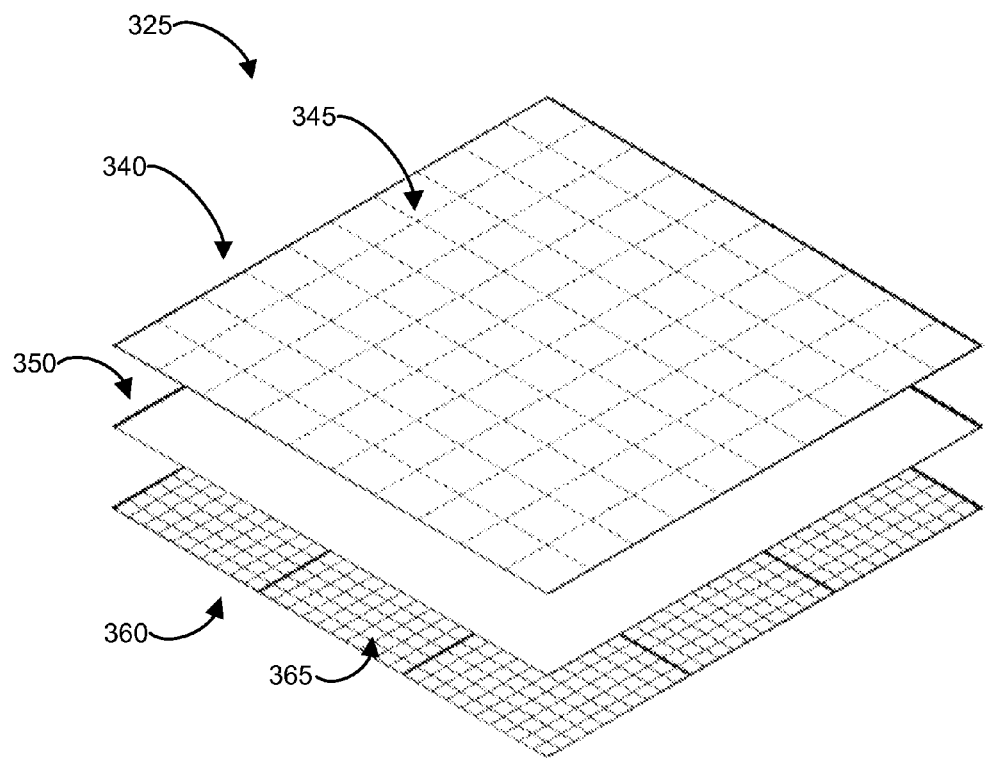
FIG. 4 illustrates a perspective view a portion of a multi-resolution pixelated detector.

FIG. 4 illustrates a perspective view of the multi-resolution pixelated detector 325 without the detector housing 370 or the beam entrance 380. The pixelated electrodes 340, 360 and the high voltage plane 350 are arranged as parallel planes with gas gaps defined therebetween. The distance between the pixelated electrodes 340, 360 and the high voltage plane 350 can be controlled with high accuracy to provide an accurate readout. The respective pixel patterns 345, 365 on pixelated electrodes 340, 360 are arranged to face the high voltage plane 350. The pixel pattern 345 on the pixelated electrode 340 shown as dashed lines is thus on the underside of the plane in the view illustrated in FIG. 4. As illustrated, the first pixelated electrode 340 has a lower resolution than the second pixelated electrode 360. It is noted that the first pixelated electrode 340 can have a higher resolution than the second pixelated electrode 360, as discussed above.

The relatively small beam trajectory angles noted above and the small distance between the center of the first gas gap 342 and the center of the second gas gap 346 mean that the effect of a non-zero trajectory angle of deflected charged particle pencil beam 300' is negligible. In other words, the projection of the deflected charged particle pencil beam 300', including the projection of the transverse beam intensity distribution, onto electrodes 340 and 360 can be considered identical. The distance between the centers of the gas gaps can be between 5 mm and 25 mm.

Pixelated ionization detector chambers are also described in U.S. Patent Application Publication No. 2014/0265823, which is assigned to the same assignees of record and hereby incorporated herein by reference. It is noted that each pixelated electrode 340, 360 can be in a separate housing with its own ionization chamber (gas gap and high voltage plane), as known in the art, instead of the integrated configuration illustrated in FIGS. 3 and 4. In this case the effect of trajectory angle may not be negligible, depending on the separation. If the trajectory angle is known, for example from the settings of the magnetic field generator, then a mathematical correction can be applied to compensate the resulting offset in x axis and/or y axis between the transverse beam intensity centroids that are projected on to the first and second pixelated electrodes.

The first pixelated electrode 340 has an array of pixels having larger pixel dimensions (e.g., lower resolution). For example, the first pixelated electrode 340 can have a pixel center spacing between about 5 mm and about 10 mm. The output signals from the first resolution pixelated electrode 340 can be used to determine the centroid of the transverse beam intensity distribution of the charged particle pencil beam 100' using calculations known to those skilled in the art. In some embodiments, the first pixelated electrode 340 has the same number of pixels as each sub-array of the higher resolution pixelated detector 360.

The second pixelated electrode 360, which has smaller pixel dimensions (e.g., higher resolution), includes an array of pixels that are divided into a plurality of sub-arrays formed of pixels that are electrically connected in parallel at respective pixel locations, as described below. Each such parallel connection is connected to an electronic readout channel. The pixels are defined by electrode elements disposed in a rectangular pattern in a plane substantially perpendicular (e.g., an x-y plane) to the direction of travel of the charged particle pencil beam (e.g., charged particle pencil beam 100). The elements can be spaced apart in regular or irregular intervals in the x and y directions to define pixels. In some embodiments, the centers of the pixels are spaced apart about 1.0-5.0 mm. In some embodiments the insulating gaps between electrode elements are made about 0.02 to 0.10 mm wide. The pixel elements collect a current formed when the deflected charged particle pencil beam 100' creates ion-electron pairs in an adjacent gas gap (e.g., second gas gap 346) with an electric field as known in the art. The second pixelated electrode 360 is configured to generate a second output signal data array that represents the pixel by pixel combined electrical output of each sub-array, as described below.

Figure 5:
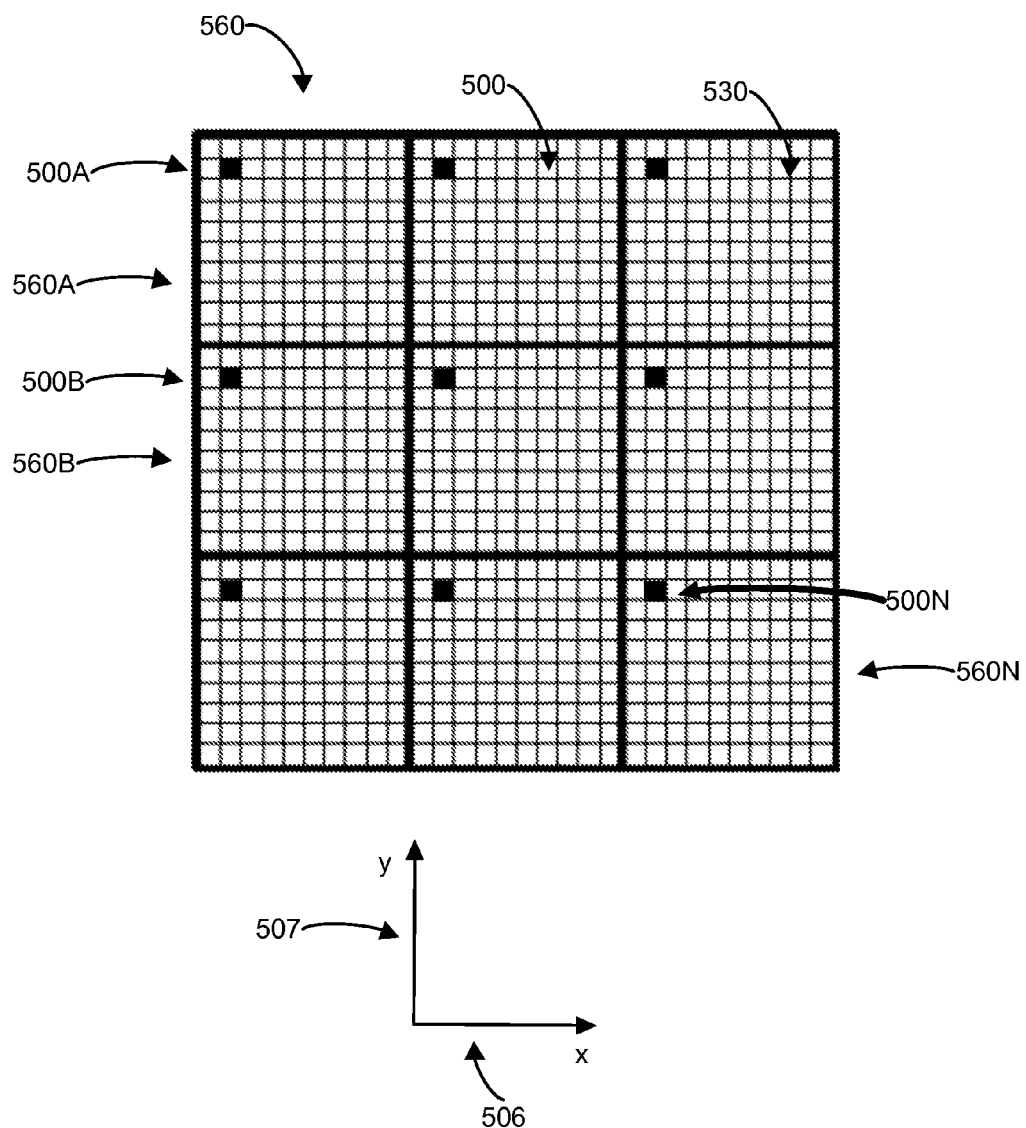
FIG. 5 illustrates a plan view of a high-resolution pixelated readout electrode plane comprised of multiple sub-arrays.

FIG. 5 illustrates a plan view of a high-resolution pixelated electrode 560. The high-resolution pixelated electrode 560 includes a plurality of pixels 500 of accurately known size and position. The pixels 500 can have identical or substantially identical dimensions. For example, the pixels 500 can be about 2 mm in a first direction parallel to a first axis 506 (e.g., an x-axis) and about 2 mm in second direction parallel to a second axis 507 (e.g., a y-axis), which is orthogonal to the first direction. The pixel elements are defined by detector elements 530. One skilled in the art would recognize that other resolutions for the high-resolution pixelated detector 560 can be used, such as about 1 mm, about 1.5 mm, about 2.5 mm, about 3 mm, etc.

The high-resolution pixelated electrode 560 is divided into sub-arrays 560A, 560B . . . 560N (in general, sub-array(s) 560$n$). As illustrated, the sub-arrays 560$n$ are equal in size in the first and second directions 506, 507. In some embodiments, the sub-arrays 560$n$ have different sizes. The sub-arrays 560$n$ can be larger than or equal to the size of the beam spot. For example, the sub-arrays 560$n$ can be larger than or equal to the area of the beam spot that represents between about 95% to about 99% of the total beam intensity.

The respective pixels 500 of sub-arrays 560$n$ are electrically connected in parallel with one another. As such, a pixel 500A at a given column and row (i, j) in sub-array 560A is electrically connected to a pixels 500B, 500N at an equivalent location (i, j) in sub-arrays 560B, 500N, respectively, and generally to a pixel 500$n$ at an equivalent location (i, j) in sub-array 560$n$. The pixels 500$n$ can be electrically connected using an internal trace on a printed circuit board or similar configuration. Alternatively, the pixels 500$n$ can be electrically connected using external wiring. When a current from a beam spot is detected from a connection to a pixel 500$n$, which includes the parallel-connected pixels 500A, 500B . . . 500N, at (i, j), it is not known from which sub-array 560$n$ the current originated. In other words, without more information, one cannot determine from the electrical readout which pixel 560$n$ over the whole electrode 560 area detected the current.

Figure 6:
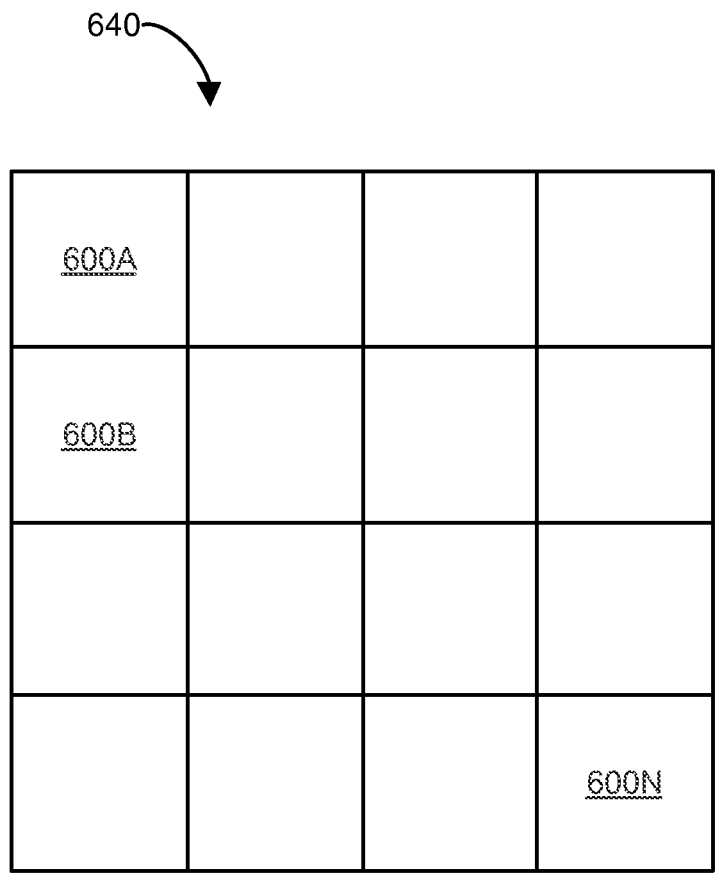
FIG. 6 illustrates a plan view of a low-resolution pixelated readout electrode plane.
Figure 6:
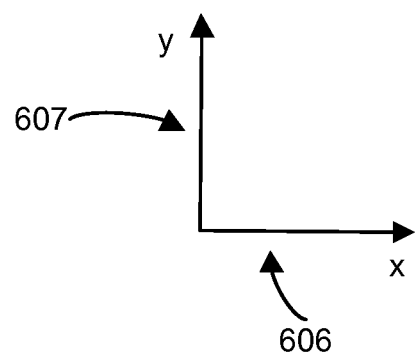

FIG. 6 illustrates a plan view of a low-resolution pixelated electrode 640. The low-resolution pixelated electrode 640 includes a plurality of pixels 600A, 600B . . . 600N (generally referred to as pixel(s) 600$n$). The pixels 600$n$ can have an accurately-known size and position. For example, pixel 600$n$ can be about 8 mm in a first direction parallel to a first axis 606 (e.g., an x-axis) and about 8 mm in second direction parallel to a second axis 607 (e.g., a y-axis), which is orthogonal to the first direction. One skilled in the art would recognize that other resolutions for the low-resolution pixelated electrode 340 can be used, such as about 7 mm, about 7.5 mm, about 7.8 mm, about 8 mm, etc. In some embodiments, the low-resolution pixelated electrode 640 has the same number of pixels 600$n$ as each sub-array (e.g., sub-array 560$n$) of the high resolution electrode.

When a current is detected from a given pixel 600$n$, the electrical readout of electrode 640 can be used to determine which pixel(s) 600$n$ detected the current without ambiguity. A provisional centroid of the transverse beam intensity distribution of the charged particle pencil beam can be made from the signals in all pixels 600$n$ using calculations known to those skilled in the art.

Referring back to FIG. 2, the detector control system 285 receives as inputs a first output signal from the first pixelated electrode (e.g., first pixelated electrode 340) of detector system 280 to create a first data array and a second output signal from the second pixelated electrode (e.g., second pixelated electrode 360) of detector system 280 to create a second data array. Since the second output signal represents the combined electrical output of each pixel location in each sub-array (e.g., sub-array 360$n$), there is an ambiguity as to the physical location of the pixels that detected the current (and thus the physical location of the charged particle pencil beam 100'), as described above. This manifests as two effects. The first effect is that it is not known which of the N sub-arrays the beam intensity distribution centroid is located in. The second effect is that if the beam intensity distribution extends over more than one sub-array, the distribution will appear to "wrap around" in the first output signal due to the parallel-connected pixels (e.g., pixels 500$n$). The detector control system 285 can resolve this ambiguity and allow perfect reconstruction of the beam intensity profile at the resolution provided by the higher resolution electrode by using the first data array from the lower resolution pixelated electrode. In general, the lateral beam intensity distribution should not exceed the dimensions of the sub-arrays.

Figure 7:
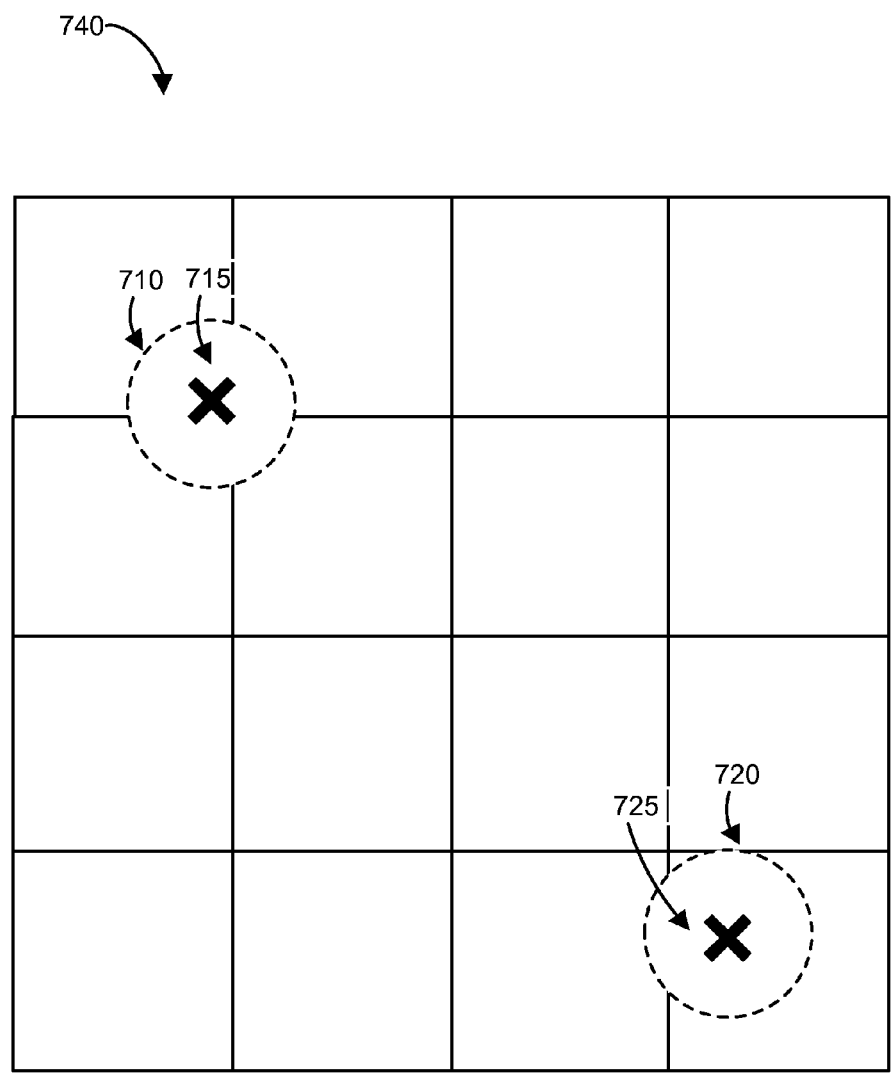
FIG. 7 illustrates exemplary transverse intensity distributions, or "spots" of a charged particle pencil beam projected onto a low-resolution pixelated electrode.

FIG. 7 shows a first and second beam spot 710, 720 (i.e., transverse intensity distributions) projected onto a lower-resolution electrode 740. The first and second beam spots 705, 710 represent spots of a beam from different time periods. Although not illustrated, it is noted that beam spots can have a non-uniform transverse intensity distribution and they can have a variable and/or irregular shape. The low-resolution electrode signals are calculated to give centroid positions 715 and 725, respectively, in physical space using methods known in the art. The calculated centroid positions 715, 725 may not be perfect due to the relatively larger pixel size and thus coarse sampling of the continuous beam intensity distribution, but it is adequate to assign the beam centroid positions 715, 725 to one of the high resolution electrode sub-arrays as described above. In the unlikely event that the centroid positions 715, 725 falls exactly on the division between two or four electrodes, then the selection of sub-array can be arbitrary with no loss of accuracy. For example the lower-numbered sub-array can be selected in such a circumstance.

If the deflected charged particle pencil beam has a significant beam trajectory angle, in other words the beam is not orthogonal to the planes of electrodes 340 and 360, so that the centroid is significantly displaced in physical space between the low resolution and high resolution electrodes, then this may be compensated by simple calculation if the angle and the separation between the centers of the gas gaps 342 and 346 is known by other means, as described above. If this is not possible, then the method described will still give correct results but with a reduction in the maximum extents of the beam intensity distribution that can be reconstructed.

Figure 8:
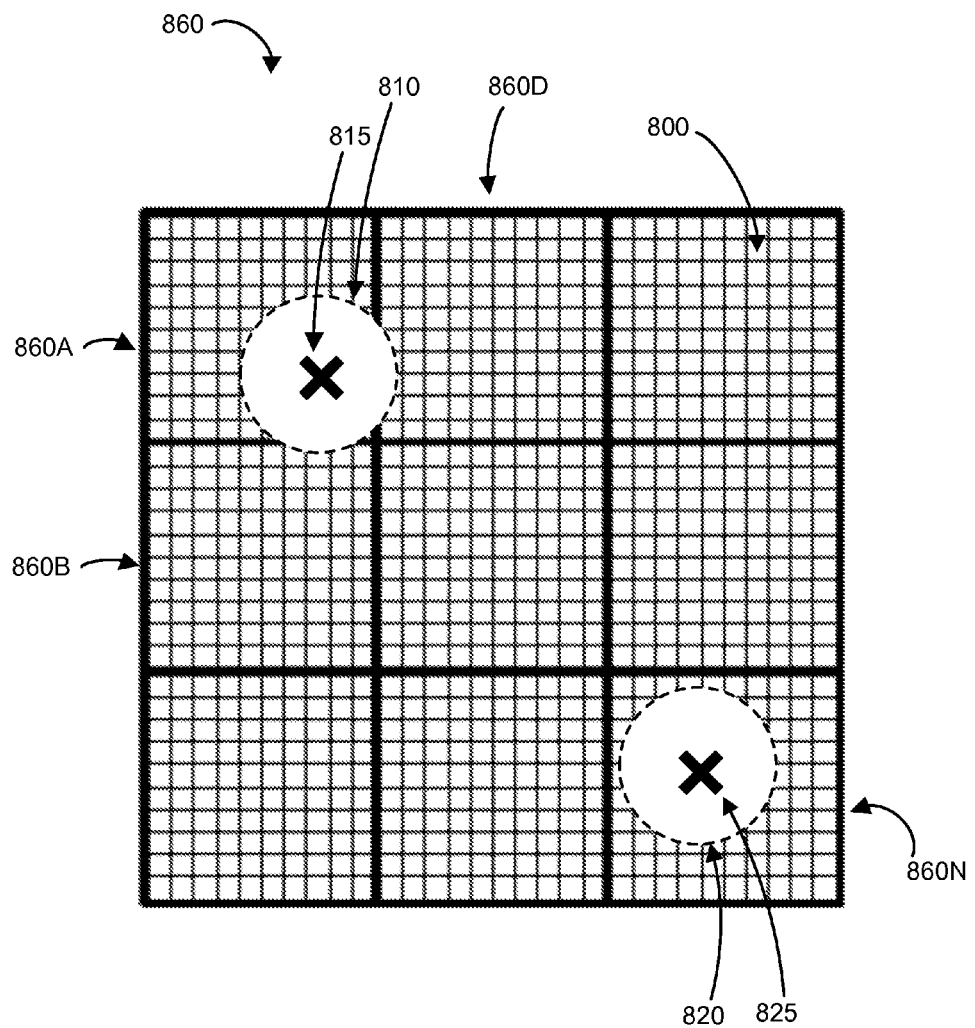
FIG. 8 illustrates exemplary spots of a charged particle pencil beam projected onto a high-resolution pixelated electrode.

FIG. 8 illustrates beam spots 810, 820, which are the beam spots 710, 720 superimposed onto the geometry of the high-resolution electrode 860. The centroid positions 815, 825 are the centroid positions 715 and 725 determined from output of the low-resolution electrode 740 and then superimposed onto the geometry of the high-resolution electrode 860. The respective centroid positions 815, 825 are each located in a sub-array 360n, and in particular in sub-arrays 860A and 860N for the cases illustrated in FIG. 8.

If the beam spot size is contained entirely in the extents of a sub-array such as case of spot 820 in sub-array 860N, then no reconstruction of the beam intensity profile is needed. For example, the spot 820 can be located within sub-array 860N if the approximate centroid 825 is located within one pixel of the center of sub-array 860N. The physical location of the beam spot (and beam intensity profile) is known without ambiguity because the absolute physical locations of each pixel in the sub-array 860N are known. A complete high resolution data array may be constructed by assigning the value zero (or other nominal value) to all other pixels 800 that are not in the sub-array 860N. Alternatively, the values of pixels 800 that are not in the sub-array 860N can be set by using information from the output of the low-resolution pixelated detector. For example, the current density from pixels that are not in the sub-array 860F at positions (x, y) can be made equal to the measured current density from the low resolution array pixels that have positions (x', y') that are closest to (x, y).

A more accurate centroid may now be calculated from the output of the high-resolution electrode, and more precise calculations of the width and shape of the beam intensity distribution can be made.

If the beam intensity distribution lies over two, three or four abutting sub-arrays, then the individual current signals that constitute the high resolution electrode signal must be re-mapped to obtain their correct relative positions in physical space. For example, the beam spot 810 lies over three abutting sub-arrays 860A, 860B, and 860D.

Figure 9:
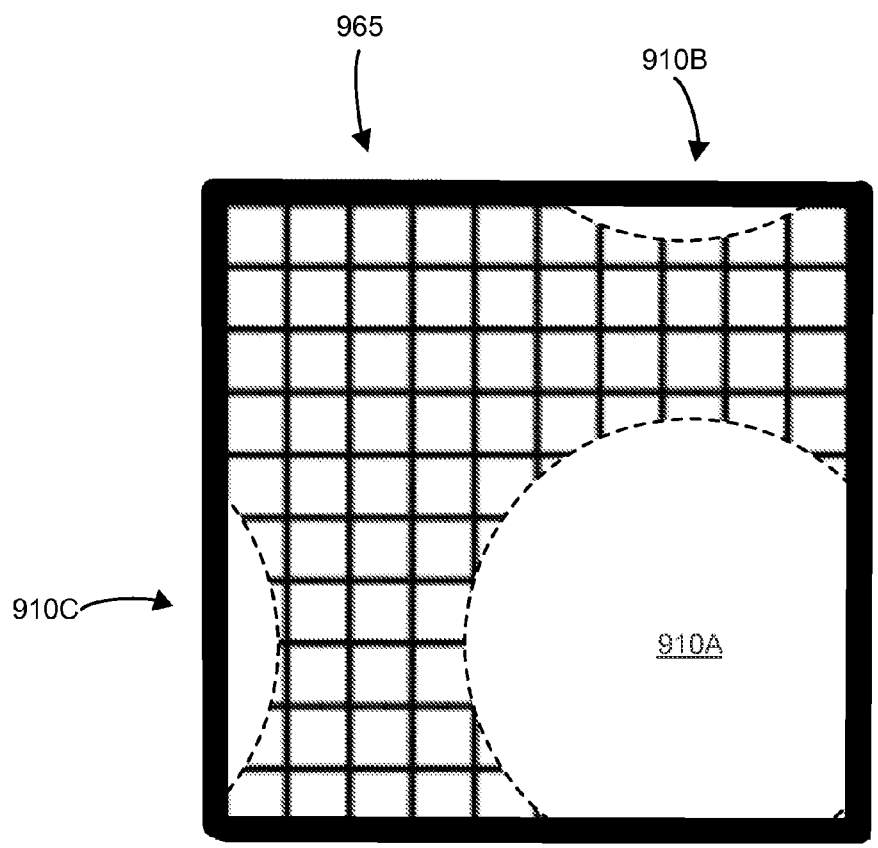
FIG. 9 illustrates a representation of an electronic data array resulting from the readout of a high-resolution pixelated electrode.

FIG. 9 illustrates how the beam intensity distribution appears to "wrap around" high-resolution electrode data array 965 due to the parallel connection of corresponding pixels 800 in the sub-arrays 860n of the high-resolution electrode 860. A first beam spot portion 910A corresponds to the portion of beam spot 810 that lies in sub-array 860A, as illustrated in FIG. 9. A second beam spot portion 910B corresponds to the portion of beam spot 810 that lies in sub-array 860B. A third beam spot portion 910C corresponds to the portion of beam spot 810 that lies in sub-array 860C.

Figure 10:
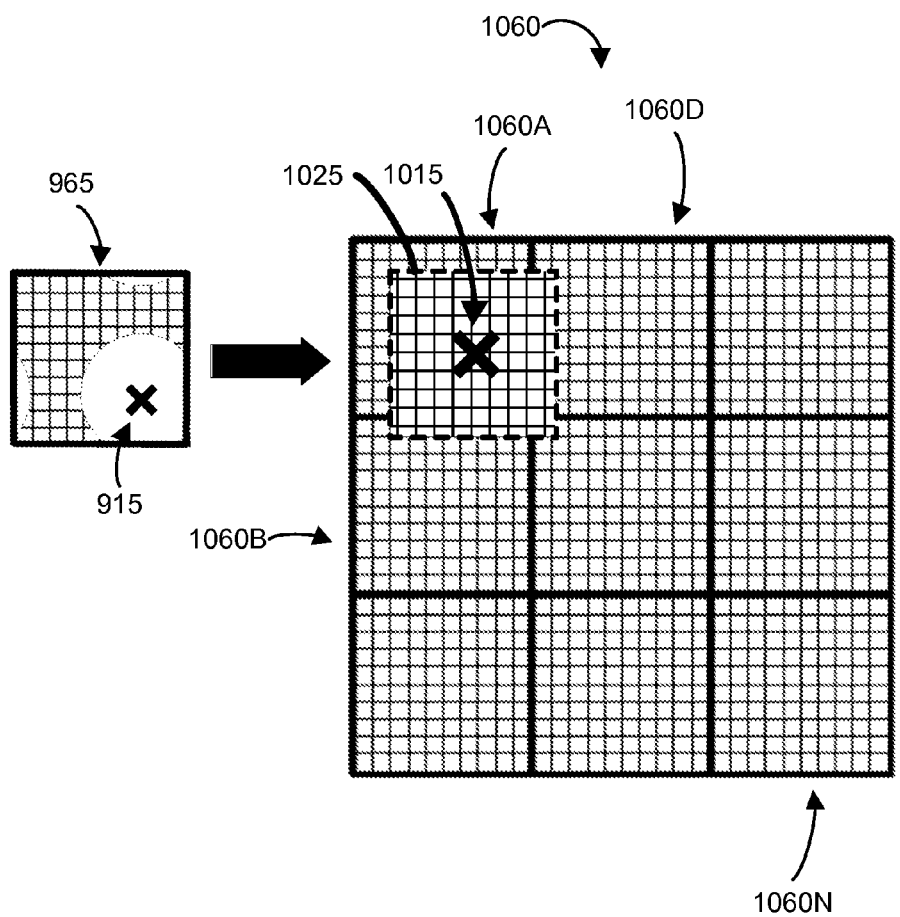
FIG. 10 illustrates the process of mapping the high-resolution electrode data array onto the physical pixels of high-resolution pixelated electrode

FIG. 10 illustrates the process of mapping the high-resolution electrode data array 965 onto the physical pixels of high-resolution pixelated electrode 1060. Analytically, an electronic data array 1025 is centered on centroid position 1015, which was calculated using the output of the low-resolution electrode as described above. The electronic data array 1025 has the same dimensions as the sub-arrays 1060n. The high-resolution electrode data array 965 is superimposed on the electronic data array 1025 by aligning the respective centroid positions 915, 1015.

Figure 11:
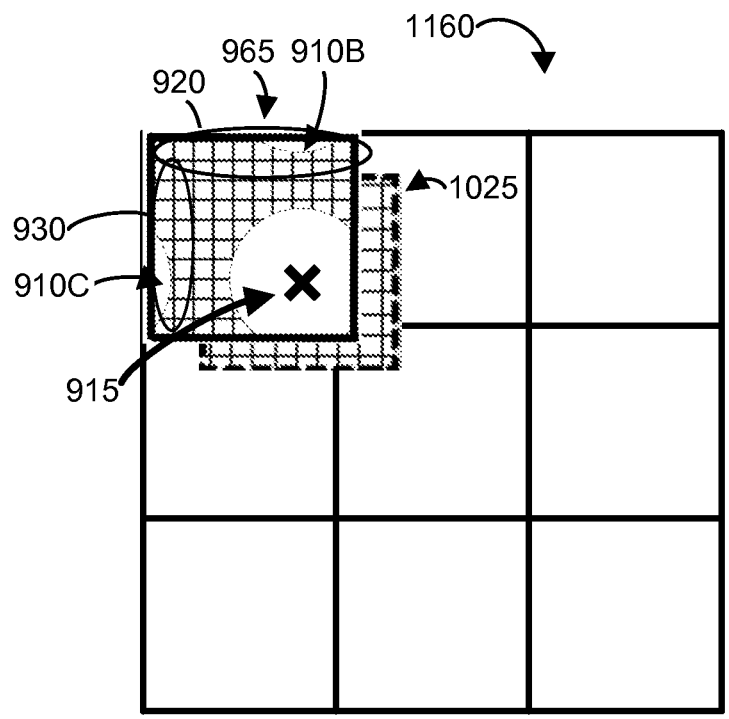
FIG. 11 illustrates the superimposed data arrays described in FIG. 10.

FIG. 11 illustrates the superimposed data arrays described in FIG. 10. As described above, high-resolution electrode data array 965 is superimposed on the electronic data array 1025 by aligning the respective centroid positions 915, 1015 (centroid position 1015 is not illustrated in FIG. 11) on a representation of high-resolution electrode 1060. In the aligned position, sub-portions 920, 930 of the high-resolution electrode data array 965 fall outside the boundaries of electronic data array 1025. The beam spot portions 910B, 910C in sub-portions 920, 930, respectively, are the "wrap-around" beam intensity distribution described above. By re-mapping or offsetting the beam spot portions 910B, 910C, the beam spot can be reconstructed at the high resolution provided in high-resolution electrode 1160. It is noted that pixel gridlines are not illustrated in FIG. 11 for clarity.

Figure 12:
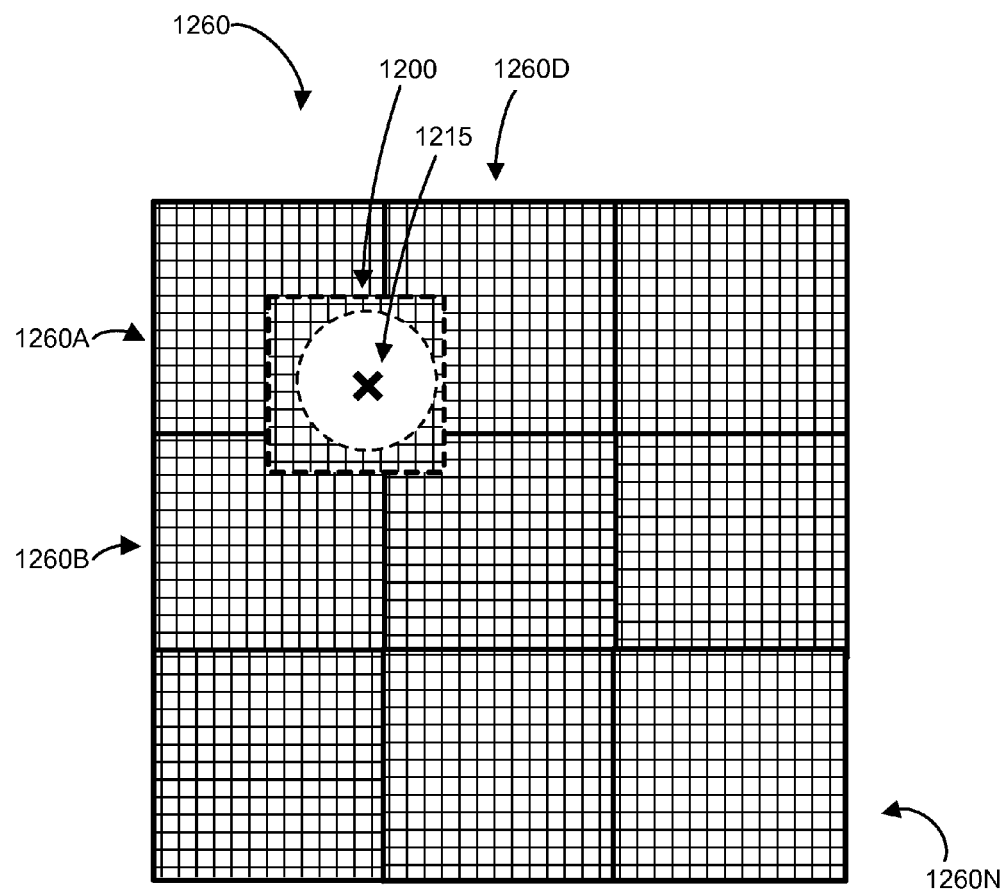
FIG. 12 illustrates how the reconstructed beam profile is located on a complete high-resolution readout plane.

FIG. 12 illustrates how the re-mapped electronic data array 1200 can be associated with the pixels of the high resolution electrode 1260 such that an absolute physical position is assigned to each data array element to produce a reconstructed high-resolution data array. A more accurate centroid 1215 may now be calculated from the reconstructed high-resolution data array, and more precise calculations of the width and shape of the beam intensity distribution can be made. Elements in the reconstructed high-resolution data array that are not included in re-mapped data array 1200 can be assigned the value zero. Alternatively the values of pixels that are not in re-mapped electronic data array 1200 can be set by using information from the low resolution data array. For example, the current density from pixels that are not in the re-mapped data array 1100 at positions (x, y) can be made equal to the measured current density from the low resolution array pixels that have positions (x', y') that are closest to (x, y).

The measured values from detector system 180 and readout system 185 may be used for quality assurance of the particle beam therapy system.

It will be evident that the technology may also be applied to the detector(s) 140 and control system 170 illustrated in FIG. 1. Control system 170 can use values calculated from high-resolution data representing the centroid, width, shape and total current of the signals created by the deflected charged particle pencil beam 100' to more accurately control the deflected charged particle pencil beam 100'. As illustrated in FIG. 1, feedback control loops are provided between the control system 170, the charged particle pencil beam generator 110, and the magnetic field generator 130 to control the energy, dosage (intensity and/or dosage time), and/or deflection angles of the charged particle pencil beam. In some embodiments, the control system 170 is in communication with a beam control unit. The beam control unit can receive a signal from the control system 170 that represents the actual position/location, shape, and charge density of the spot. The beam control unit can generate feedback controls to the charged particle pencil beam generator 110 and/or the magnetic field generator 130 as discussed above.

Figure 13:
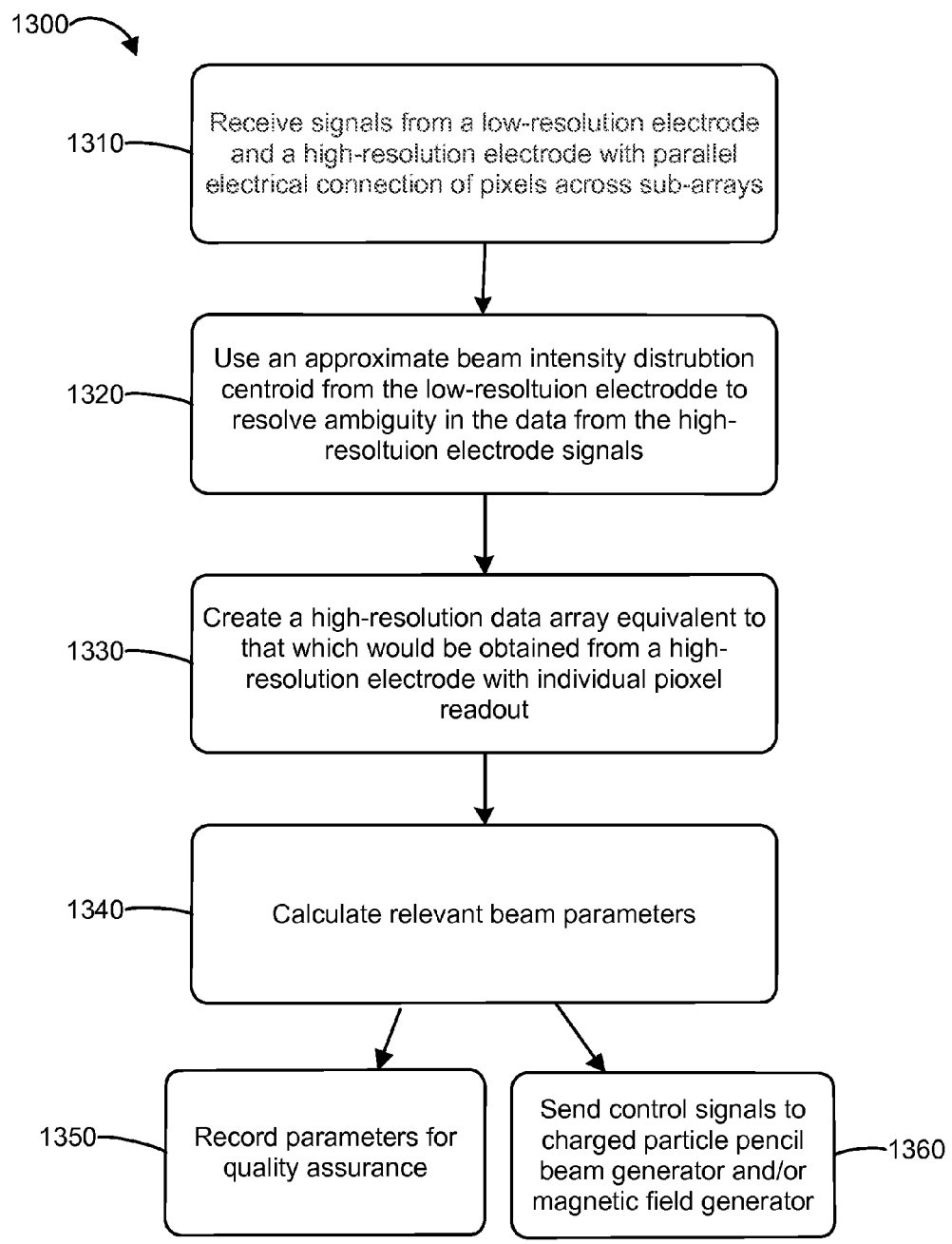
FIG. 13 is a flow chart that illustrates for an exemplary method of collecting quality assurance data and for controlling a charged particle pencil beam system.

FIG. 13 is a flow chart 1300 that illustrates an exemplary method of measuring the performance of and controlling a charged particle pencil beam system. In 1310, signals are received from low- and high-resolution pixelated electrodes as described above. In 1320, an approximate centroid transverse intensity distribution of the charged particle beam is determined with electrical output data from the low-resolution electrode. This centroid is used to remove ambiguity from the electrical output data received from the high resolution electrode. In 1330, a complete high-resolution data array representation of the beam intensity profile is assembled representing the whole area of the high resolution pixelated electrode, equivalent to that which would have been received from a high resolution electrode having individual readout of each pixel. In 1340 this high resolution data array is used to calculate relevant beam parameters, such as the position and the transverse intensity distribution. In 1350 this information is used as quality assurance information for the effective operation of the particle therapy equipment. In 1360 this information is used for feedback control to enhance the accuracy in the position, intensity distribution and integrated intensity of the particle beam.

While reference has been made to pixelated electrodes, it is noted that alternative detectors can be used in place of the pixelated detectors. For example, a horizontal strip electrode and a vertical strip electrode, as known in the art, can be used in place of the high-resolution pixelated detector and/or the low-resolution pixelated detector. The strip detectors can have the same resolution as the respective high- or low-resolution pixelated detectors.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. A system for detecting a characteristic of a charged particle pencil beam, the system comprising:
    a multi-resolution detector disposed proximal to an isocenter plane, said multi-resolution detector comprising:
        a first pixelated electrode comprising a plurality of sub-arrays of first pixels, wherein each respective first pixel at each relative position in each sub-array is electrically connected in parallel with one another, such that said first pixelated electrode dynamically generates a first output representing a combined electrical output of said respective first pixels from said sub-arrays, said first pixels detecting an electrical current created by said charged particle pencil beam;
        a second pixelated electrode comprising a plurality of second pixels, said second pixelated electrode configured to dynamically generate a second output representative of an approximate physical position of the charged particle pencil beam in a plane substantially parallel to said isocenter plane, said second pixelated electrode having a second resolution less than a first resolution of said first pixelated electrode; and
        a high-voltage plane disposed between said first and second pixelated electrodes;
    a diagnostic control system comprising a memory and a processor, the diagnostic control system configured to receive as inputs the first output and the second output and to determine an actual position and an actual transverse intensity distribution of said charged particle beam based on said first and second outputs, said actual position and said actual intensity distribution having said first resolution.

2. The system of claim 1, wherein said diagnostic control system is configured to transmit said actual position and said actual intensity distribution to a beam control system.

3. The system of claim 2, wherein said beam control system updates a calibration parameter based on at least one of said actual position and said actual intensity distribution.

4. The system of claim 1, wherein a first gas gap is defined between said first pixelated electrode and said high voltage plane.

5. The system of claim 4, wherein a second gas gap is defined between said high voltage plane and said second pixelated electrode.

6. The system of claim 1, wherein said first pixel has a first size and said second pixel has a second size, said first size less than said second size.

7. The system of claim 1, wherein said first pixelated electrode is disposed in a first plane and said second pixelated electrode is disposed in a second plane such that said first plane, said second plane, and said high-voltage plane are substantially parallel to said isocenter plane.

8. A system for detecting a characteristic of a charged particle pencil beam, the system comprising:
    a multi-resolution detector system disposed proximal to an isocenter plane, said multi-resolution detector comprising:
        a first pixelated detector comprising a first pixelated electrode having a plurality of sub-arrays of first pixels, wherein each respective first pixel at each relative position in each sub-array is electrically connected in parallel with one another, such that said first pixelated detector dynamically generates a first output representing a combined electrical output of said respective first pixels from said sub-arrays, said first pixels detecting an electrical current created by said charged particle pencil beam; and
        a second pixelated detector comprising a second pixelated electrode having a plurality of second pixels, said second pixelated detector configured to dynamically generate a second output representative of an approximate physical position of the charged particle pencil beam in a plane substantially parallel to said isocenter plane, said second pixelated electrode having a second resolution less than a first resolution of said first pixelated electrode;
    a diagnostic control system comprising a processor, the control system configured to receive as inputs the first output and the second output and to determine an actual position and an actual transverse intensity distribution of said charged particle beam based on said first and second outputs, said actual position and said actual intensity distribution having said first resolution.

9. The system of claim 8, wherein said diagnostic control system is configured to transmit said actual position and said actual intensity distribution to a beam control system.

10. The system of claim 9, wherein said beam control system updates a calibration parameter based on at least one of said actual position and said actual intensity distribution.

11. The system of claim 8, wherein a first gas gap is defined between said first pixelated electrode and said high voltage plane.

12. The system of claim 11, wherein a second gas gap is defined between said high voltage plane and said second pixelated electrode.

13. The system of claim 8, wherein said first pixel has a first size and said second pixel has a second size, said first size less than said second size.

14. The system of claim 8, wherein said first pixelated electrode is disposed in a first plane and said second pixelated electrode is disposed in a second plane such that said first plane, said second plane, and said high-voltage plane are substantially parallel to said isocenter plane.

15. A method of characterizing a charged particle pencil beam, said method comprising:
    receiving a combined electrical output generated by a charged particle pencil beam with a first pixelated electrode comprising a plurality of sub-arrays of first pixels having a first resolution, wherein each respective first pixel at each relative position in each sub-array is electrically connected in parallel with one another;

determining an approximate physical position of said charged particle pencil beam with electrical output data from a second pixelated electrode, said second pixelated electrode comprising a plurality of second pixels having a second resolution, said second resolution lower than said first resolution; and calculating an actual physical position and an actual transverse intensity distribution of said charged particle pencil beam using said combined electrical output and said approximate physical position, said actual physical position and said actual transverse intensity distribution having said first resolution.

16. The method of claim 15, further comprising disposing a multi-resolution detector proximal to an isocenter plane, said multi-resolution detector comprising said first and second pixelated electrodes.

17. The method of claim 15, further comprising disposing a first pixelated detector and a second pixelated detector proximal to an isocenter plane, said first pixelated detector comprising said first pixelated electrode, said second pixelated detector comprising said second pixelated electrode.

18. The method of claim 15, further comprising updating a calibration parameter in a beam control system based on at least one of said actual physical position and said actual intensity distribution.

19. The method of claim 15, further comprising disposing a multi-resolution detector between an isocenter plane and a magnetic field generator, said multi-resolution detector comprising said first and second pixelated electrodes.

20. The method of claim 19, further comprising transmitting a control signals to a charged particle beam generator, said control signal based on at least one of said actual physical position and said actual transverse intensity distribution of said charged particle pencil beam.

21. The method of claim 19, further comprising transmitting a control signal to a magnetic field generator based on said actual location, said control signal based on at least one of said actual physical position and said actual transverse intensity distribution of said charged particle pencil beam.

22. The method of claim 19, wherein said first pixel has a first size and said second pixel has a second size, said first size less than said second size.

23. An integrated multi-resolution detector comprising:
a first pixelated electrode disposed in a first plane, said first pixelated electrode comprising a plurality of sub-arrays of first pixels, wherein each respective first pixel at each relative position in each sub-array is electrically connected in parallel with one another, such that said first pixelated electrode dynamically generates a first output representing a combined electrical output of said respective first pixels from said sub-arrays, said first pixels detecting an electrical current created by a charged particle pencil beam;

a second pixelated electrode disposed in a second plane, said second pixelated electrode comprising a plurality of second pixels, said second pixelated electrode configured to dynamically generate a second output representative of a physical position of said charged particle pencil beam in said second plane, said second pixelated electrode having a second resolution less than a first resolution of said first pixelated electrode; and a high-voltage plane disposed between said first and second pixelated electrodes, wherein said first plane, said second plane, and said high-voltage plane are substantially parallel to one another.

24. The detector of claim 23, wherein said first pixel has a first size and said second pixel has a second size, said first size less than said second size.

* * * * *